United States Patent [19]
Buck et al.

[11] Patent Number: 5,152,177
[45] Date of Patent: Oct. 6, 1992

[54] PROCESS FOR THE DETECTION AND QUANTITATION OF CORROSION AND SCALE INHIBITORS IN PRODUCED WELL FLUIDS

[75] Inventors: Erwin Buck; John B. Sudbury, both of Ponca City, Okla.

[73] Assignee: Conoco Inc., Ponca City, Okla.

[21] Appl. No.: 579,425

[22] Filed: Sep. 7, 1990

[51] Int. Cl.⁵ ............................................. G01N 30/90
[52] U.S. Cl. .................................. 73/61.54; 166/902; 166/310; 166/250
[58] Field of Search ............... 73/61.1 C; 166/279, 166/310, 902, 250; 210/198.3, 658

[56] References Cited

U.S. PATENT DOCUMENTS

| | | |
|---|---|---|
| 3,149,068 | 9/1964 | Biederman, Jr. et al. ....... 73/61.1 C |
| 3,254,959 | 6/1966 | Fallgatter et al. ................... 210/658 |
| 3,298,438 | 1/1967 | Anthony et al. ................ 166/250 X |
| 3,752,316 | 8/1973 | Takeshita .......................... 210/198.3 |
| 4,084,091 | 4/1978 | Thomas ....................... 73/61.1 C X |
| 4,665,981 | 5/1987 | Hayatdavoudi .................... 166/250 |
| 4,752,587 | 6/1988 | Dickakian .................... 73/61.1 C X |

Primary Examiner—Hezron E. Williams
Assistant Examiner—Michael J. Brock

[57] ABSTRACT

Corrosion and scale inhibitors in fluids produced from a subterranean formation are separated, detected, and quantified by thin layer chromatography through the use of selected developing solvents and visualization reagents.

18 Claims, 2 Drawing Sheets

PROCESS FOR THE DETECTION AND QUANTITATION OF CORROSION AND SCALE INHIBITORS IN PRODUCED WELL FLUIDS

BACKGROUND OF THE INVENTION

1. Field of the Invention

A useful method of applying inhibitors to producing oil wells is to displace or "squeeze" them into the producing reservoir. In the case of a corrosion inhibitor, the inhibitor provides corrosion protection to the well as the inhibitor is produced back from the formation. When the returning corrosion inhibitor concentration reaches a low level (typically 1-10 ppm), the formation must be "resqueezed."

There presently exists no analytical method, either field or laboratory, for determining inhibitor concentrations in produced fluids (i.e. oil and water) at the low levels required. In the case of corrosion inhibitors, reliance is now placed in corrosion monitoring techniques to establish when a well must be retreated. The obvious difficulty in this use of corrosion monitoring is that the well must corrode before it again receives a corrosion prevention treatment.

Returning corrosion inhibitor partitions between the liquid phases of the fluid produced from a well. The desired analytical method (or methods) thus needs to be suitable for determination of inhibitor in brines, crude oils, and condensates. What is needed is the total returning corrosion inhibitor concentration.

The corrosion inhibitor chemistry of most general interest for oil field use is the chemistry of nitrogen-containing polar organic compounds. Inhibitors are usually made from commercial intermediates that are not pure compounds. Nonetheless, the species of interest is usually one or more of the following:

1. Amines and Diamines-primary, secondary, tertiary and quaternary.
2. Amides.
3. Amino-amides.
4. Amine Salts.
5. Imidazolines.

The side chains are typically 1 to 18 $CH_2$ units long and may contain double bonds. The diamines are most frequently ethylene or propylene diamines. The final inhibitor or its precursors are sometimes ethoxylated.

The analytical method presently used in the industry for determining corrosion inhibitor content is an ion pair technique suitable for measuring corrosion inhibitors in water with a detection limit of about 5 ppm. The essence of the technique is the addition of an excess of a large anionic molecule to the water containing the cationic corrosion inhibitor. The ion pair formed is then extracted into a solvent and its concentration determined colorometrically.

The first obvious limitation of the ion pair technique is that it detects all large cationic molecules, i.e., it is neither specific for nor all inclusive for corrosion inhibitors. The second difficulty is that the method is useful for aqueous systems only. To determine inhibitor concentration in the oil phase, the inhibitor must be extracted from the oil into water before the ion pair technique can be used. Not only is the extraction difficult, but many other crude oil components are also extracted and therefore interfere with the final determinations.

2. The Prior Art

U.S. Pat. No. 4,665,981 issued to Hayatdavoudi relates to a method and apparatus for inhibiting corrosion of well tubing by monitoring the concentration of corrosive element therein with a conventional transducer and using a computer system to optimize the rate of injection of said inhibitor responsive to the monitored condition.

U.S. Pat. No. 3,298,438 issued to Anthony et al. discloses a method for preventing corrosion of metallic surfaces that are exposed to corrosive vapors by conducting analytical measurements using chromatographs specially designed for measuring the inhibitor and the acid gas content.

SUMMARY OF THE INVENTION

In accordance with this invention, a corrosion or scale inhibitor in a fluid produced from a subterranean formation is detected and quantified by evaluating the fluid with thin layer chromatography (TLC) using one or more developing solvents with which the inhibitor is selectively separated from the produced fluid on a sorbent, and then visualizing the separated inhibitor and thereafter comparing the visualized inhibitor with standard concentrations of inhibitor.

DETAILED DESCRIPTION OF THE INVENTION

Figure 1:
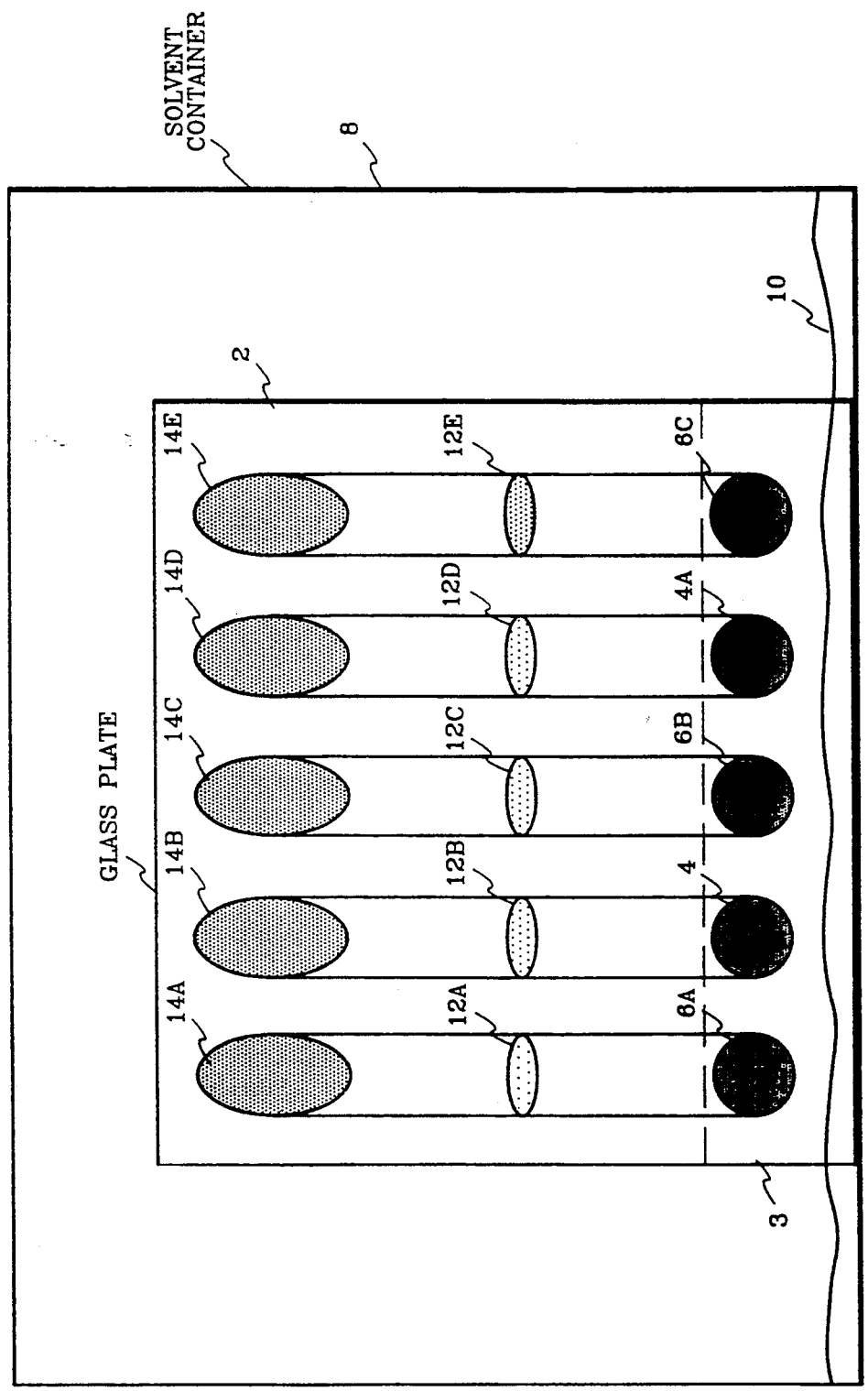
FIG. 1 is a schematic diagram of visualized chromatograms.

The process of the invention is directed to determining the amount of corrosion or scale inhibitor contained in a fluid produced from a subterranean formation, usually an oil-bearing formation. When the level of inhibitor present reaches a certain minimum value, it is necessary to increase the inhibitor concentration in the formation by introducing additional inhibitor thereto. Hence, accurate determination of the amount of inhibitor present makes it possible to reduce the amount of inhibitor used and at the same time assures that sufficient inhibitor is in the formation at all times to minimize corrosion or scale formation.

Fluids produced from subterranean formations differ in composition depending on the particular formation. For example, in some formations the produced fluid is essentially all oil, although it may contain a minor amount of water. Other formations produce a mixture of oil and water in which the amount of water may be relatively small or may be equal to or even greater than the amount of oil produced. As mentioned previously, the produced oil is usually crude oil; however, in a gas-bearing formation the produced fluid may be condensate, i.e., a mixture of lighter hydrocarbons, and such condensate may or may not be associated with various quantities of water.

It is desirable to dilute the hydrocarbon phase of the produced fluid in solvent in order to improve resolution in the thin layer chromatogram. This dilution may be performed by adding a known amount of solvent to a sample of the hydrocarbon, such as preparing a 10% solution (wt./vol.). The amount of solvent added to the hydrocarbon sample will usually be 90% although it may vary from one to about 99 volumes of solvent per volume of hydrocarbon, with the greater amounts of solvents being added to samples of heavier hydrocarbon. If the hydrocarbon phase is a condensate rather than a crude oil, the amount of solvent added to dilute the condensate may be relatively small. Where the produced fluid to be processed to determine inhibitor content is brine or water, the sample is most often run without dilution.

The thin layer chromatograms are prepared on a thin layer of sorbent, such as silica gel, alumina, reverse phase, kieselguhr, cellulose, etc., on a flat plate, usually made of glass although aluminum or plastic may also be used. The plates used are most commonly 20 centimeters square, although smaller plates can be used. To enable loading greater sample volumes, a portion of the plate near one edge is coated with a weakly absorbent material (such as kieselguhr) to provide a preabsorbent zone for application of the sample (or solution) of formation fluid. A typical example of a plate would be one having a sorbent layer of silica gel G with a preabsorbent zone of kieselguhr.

The first step in the preparation of the chromatogram is to apply a sample of the produced fluid to the thin layer chromatographic plate preabsorbent zone. The sample is applied as a spot usually by the use of capillaries or a glass barreled syringe in order to apply a small amount of the produced fluid at a time. Slow application minimizes excessive spreading of the sample application point. To apply large volumes of samples, it is usually necessary to carry out this procedure as a series of steps and allow the applied sample carrier solvent to dry thoroughly before each successive application. In order to reduce the time required to apply the complete sample, drying may be accelerated by the application of heat provided that care is taken not to adversely affect the stability of the inhibitor contained in the sample. The amount of sample applied to the plate will vary depending on the produced fluid which is being tested and the amount of inhibitor in such fluid. Sample size can be as low as one microliter or as high as 1000 microliters or more. Usually the amount of sample solution used is between about 16 and about 100 microliters.

In order to quantitatively determine the amount of inhibitor in the sample, it is necessary to provide a standard for comparison. This standard may be obtained by placing a known amount of inhibitor in the virgin produced fluid (or by the method of standard addition), the inhibitor and the produced fluid being the same as those contained in the sample to be tested. The standard sample is then placed on the TLC plate along side of the sample(s) being evaluated. The same amount of the standard material is applied as the sample, and it is applied in the same manner as the sample being analyzed. There is usually room on the plate for several samples to be processed simultaneously; therefore, multiple samples of the produced fluid and two or more standards can be applied to the same plate.

After the desired volume of sample and standard solution has been applied to the layer, the chromatograms are developed through the use of one or more solvent systems. The solvent is provided in a sealable container of sufficient size so that the lower edge of the plate may be lowered into the body of liquid solvent and the container resealed. In order to provide even movement of the solvent front on the layer and thus uniform development of the sample chromatograms, the plate is usually placed in the vapor space above the solvent for a period of time so the sorbent layer will reach equilibrium with the solvent vapor in the container. The plate is then lowered so that the liquid solvent contacts the layer below the samples. The solvent then migrates through the layer of sorbent material from bottom to top by capillary action. When this occurs the sample components are separated from each other as they partition between the immobile sorbent and the mobile solvent. The success and extent of the separation achieved depends on the similarity of the components and their relative interactions with the sorbent and solvent.

A wide variety of corrosion and scale inhibitors may be used in the practice of the invention. Typical examples of corrosion inhibitors include acetylenic alcohols; alkyl/aryl pyridines; imines; amines; imides; quaternary amines; imidazolines with a primary amine side chain of 16 to 20 carbons as the acetate, phosphate, or sulfonate salt; salts of imidazolines with dimer/trimer organic acids, e.g., of linoleic acid—the acids are commercially available as, for example, Century D-75; alkyl propyl diamines where the alkyl is from about $C_{12}$ to about $C_{20}$, a commercial example being Armour DUOMEEN T; salts and quats of alkyl propyl diamines, especially the acetate, oleate, salicylate, and with dimer/trimer acids, such as, above; ethoxylated or propyloxylated derivatives of all above; and polyimides with side chains of $C_{12}$ to $C_{20}$.

Structural formulas of some of the nitrogen containing inhibitors are as follows:

Imidazolines:

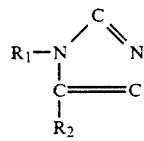

where $R_1$ and/or $R_2$ are branched or
straight chain $C_{12}$-$C_{20}$, or $(CH_2)_x$—$NH_2$
where x is typically 1 to 20. The
inhibitors may also be the salts
and the quarternaries of these
compounds Ethoxylated Amines:

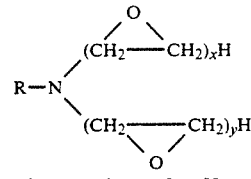

where x and y are 5 to 55

Ethoxylated Diamines:

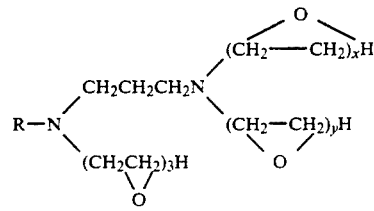

where x, y, z are 5 to 55

Ethyloxylated Amides:

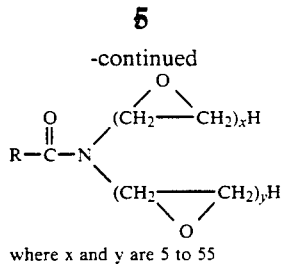

where x and y are 5 to 55

The foregoing examples of corrosion inhibitors are merely illustrative of the materials which may be used in the process of the invention, and should not be considered limiting. Other inhibitors which may be used are the sulfur and oxygen analogues of the above described nitrogen compounds. Also phosphate esters and phosphonium compounds are frequently used as corrosion inhibitors.

Many of the corrosion inhibitors are available under trade names, such as the following: VISCO corrosion inhibitors from Nalco Corporation; KONTOL corrosion inhibitors by Tretolite, a Division of Petrolite; Exxon Chemicals' COREXIT corrosion inhibitors; HAI series of acid inhibitors from Halliburton; A-250 series of acid inhibitors from Dowell-Schlumberger; Witco Chemicals' WITCAMINES; DUOMEEN series of inhibitors from Armak Chemicals, and ETHODUOMEEN from Armak Chemicals.

Scale inhibitors used in the process of the invention are commercially available under such trade names as Armak ARMOGUARD, Petrolite KONTOL, Nalco VISCO etc. The two most common classes of scale inhibitors are polyacrylates (typically with molecular weights of 2000 to 3000) and polyphosphonates, such as amino trimethylene phosphonate. The general structural formula of these phosphonates is as follows:

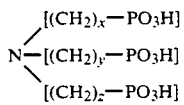

where x, y and z vary from 1 to about 12.

The foregoing scale inhibitors are merely illustrative of those which may be used in the process of the invention.

The thin layer chromatographic developing solvent systems used in practicing the invention may be conveniently divided into three groups: neutral, acidic, and basic. Acidic solvents contain an added acid, such as acetic acid or hydrochloric acid; and basic solvents contain a base, such as ammonium hydroxide.

Neutral solvents include such materials as pentane, hexane, cyclohexane, toluene, methanol, benzene, xylenes, chloroform, tetrahydrofuran, petroleum ether, isooctane:ethyl acetate (97:3, v/v), benzene:ethyl acetate:acetone (100:5:1, v/v/v), toluene:heptane (9:1, v/v), chloroform:methanol (1:1, v/v), chloroform:methanol (8:2, v/v), dichloromethane:methanol (95:5, v/v) and petroleum ether:toluene (100:4, v/v).

Among the acidic solvent systems are heptane:acetic acid (95:5. v/v), isooctane:ethyl acetate:acetic acid (60:25:15, v/v/v), chloroform:methanol:acetic acid (80:20:1, v/v/v), petroleum ether:chloroform:methanol:acetic acid (200:80:20:1, v/v/v/v) and chloroform:ethyl ether:acetic acid (50:50:4, v/v/v).

Basic solvents include such solvent systems as 2-propanol:ammonium hydroxide (8:2, v/v), methyl acetate:ethanol: ammonium hydroxide (70:20:10, v/v/v), chloroform:methanol:ammonium hydroxide (150:75:1, v/v/v) and chloroform:2-propanol:ammonium hydroxide (25:50:25, v/v/v).

The foregoing solvents are merely illustrative of the materials which may be used in the process of the invention.

Development of the chromatogram may be carried out through the use of a single solvent or a mixture of solvents or several solvents applied to the chromatogram sequentially. For example, if the produced fluid is a crude oil, it will be desirable to move as much of the oil away from the sample application point as possible. A neutral solvent such as hexane may be used for this purpose to move the paraffin components of the crude oil. A stronger solvent, such as ethyl ether, may be used to move some heavier oil components, as long as this solvent does not have the effect of moving the inhibitor also.

A basic or more polar developing solvent may then be used to move the inhibitor away from the sample application point in the chromatogram. In order for the solvent front to develop evenly, the liminary equilibration period for the solvent vapor to penetrate the sorbent is provided. A basic solvent selected from those listed previously is then used to move the inhibitor out of the sample application zone.

After the final solvent development and drying of the chromatogram, the isolated inhibitor components must be visualized. There are many types of chemical reagents which can be used for this purpose. For example, if the inhibitor is an indole, it can be visualized by spraying the chromatogram with a solution of nitrous acid and then heating the chromatogram at 100° C. for 30 minutes. Indoles are then detected as red spots, and thiazole derivatives would be detected as light green spots. An example of another spray is alizarin in ethanol. When a chromatogram is sprayed with this solution, bases such as aliphatic amines and amino alcohols are detected as violet spots on a light yellow background.

Visualization can also be provided by exposing the chromatogram to 30 percent sulfur trioxide at 125° C. This procedure reduces the nonvolatile organic materials on the chromatogram to carbon which show on the white sorbent layer as black spots. Another visualization technique used is to examine the chromatogram while illuminated with ultraviolet light. A number of compounds fluoresce when examined under ultraviolet light, particularly aromatic compounds. When chromatograms are prepared on a TLC layer which contains a fluorescent indicator, some compounds show up as dark spots on a light green background when the layer is illuminated by ultraviolet light.

There are many specific visualization reagents. Most of these reagents are used to produce a colorometric reaction and many of the reagents are specific for certain functional groups such as acids, alcohols, amines, etc.; whereas others are specific for certain elements such as nitrogen, sulfur, etc.

As previously mentioned, quantitation of the inhibitor present in the produced fluid is performed by developing the thin layer chromatogram and comparing the unknown component or components of interest in the sample chromatogram to simultaneously prepared standard chromatograms. This comparison may be performed by rather elaborate methods of densitometry or by visual comparison of spot sizes and intensities. This latter method can be highly accurate if the adjacent standard spots bracket the sample spot concentration.

It is also within the scope of the invention to compare the spot size and intensity of the developed component with a chart containing printed standards. In addition, particularly in field applications, the presence or absence of a "spot" of the developed component at a prescribed location may be used as a rough guide to determine when additional inhibitor should be introduced into the formation. As used herein the phrase "comparing the visualized inhibitor with one or more standard concentrations of inhibitor" is intended to include all of the above procedures.

When the standards are prepared properly, the concentration of the inhibitor or inhibitor component can be read directly off of the visualized chromatograms. However, if the corrosion inhibitor component partitions between two phases such as oil and water, the partition coefficient of the inhibitor components between the phases and the ratio of the phase volumes must be known or determined. The partitioning coefficient must be experimentally determined for a given produced fluid/corrosion inhibitor combination, or the concentration determined in both phases.

The TLC methodology used may be either one dimensional or two dimensional. One dimensional TLC involves single or multiple chromatogram developments in one direction, i.e. the top edge of the chromatogram is always the top edge of the chromatogram.

In two-dimensional TLC the initial development is performed in the one-dimensional direction; then after drying, the plate is rotated 90° and a second development is performed in this second direction. Usually in two-dimensional TLC only one sample is analyzed and it may be difficult to bracket with standards. If the sample application is initially made at the lower left-hand corner of the layer, and the first development is performed; when the plate is rotated 90° counter clockwise for the second development, there is room for standards at the far right-hand edge of the plate prior to both first and second developments. If standards are applied prior to each development, the place where the lines drawn at right angles through the resulting standard spots meet is where that component is expected to be located in the sample 2-D chromatogram.

The major reason for the use of 2-D TLC is as a means to remove more of the sample matrix, e.g. crude oil, in order to lower the detection limit for the remaining inhibitor compound. It can also yield a better separation of the various components of the inhibitor package should they overlap in 1-D chromatogram. In 2-D TLC the same solvent may be used in both development directions or different solvents may be used in each direction, depending on the particular system which is being treated. It is also possible that a reaction may be performed (such as exposure to iodine) between developments that will chemically alter the inhibitor, enhancing its visibility or lowering its volatility.

Referring now to the figures, FIG. 1 is a schematic representation of chromatograms prepared from a crude oil sample. To prepare the chromatogram the crude oil is first diluted with an appropriate solvent such as chloroform, a mixture of chloroform and methanol, or tetrahydrofuran. The sample is applied to a 20 centimeter square glass plate 2 which has a 1000 micron silica gel G layer applied thereto. The lower portion of the plate is covered with kieselguhr which comprises the preabsorbent zone 3. Spots of the diluted crude oil are applied to the kieselguhr area of plate 2 at 4 and 4a using a glass-barreled syringe. The volume of sample used for the spot is such that several applications are necessary. Between each application the spot is allowed to dry with the application of heat to accelerate drying if desired.

Standard samples are prepared by adding 10, 25, and 40 ppm of a corrosion inhibitor to a produced fluid and thereafter diluting the standard with the same amount of the solvent used for the produced fluid sample(s). Each standard spot, with the same volume of the standard solution spotted as used for the sample, is placed on the chromatogram plate. The 10, 25 and 40 ppm standards are applied at 6a, 6b, and 6c, respectively. Here again, placement of the spots requires a series of applications with drying between each operation.

After applying the sample and standard solutions, the plate is placed in solvent container 8 containing an initial solvent 10 such as hexane. The plate is held in the vapor phase of container 8 until equilibration of the vapor with the silica gel is obtained, usually for a period of about 10 to 30 minutes. The lower portion of the plate below the spots of samples and standards is then immersed in solvent 10 to allow the solvent to move components of the sample and standard upward on the plate. Treatment of the plate with hexane is usually continued for about 30 to about 35 minutes. The plate is then placed in a second container with a different solvent e.g. 2-propanol:ammonium hydroxide (8:2 v/v). The layer is allowed to equilibrate with this second solvent in the same manner as before and then the lower edge of the plate is lowered into the solution to prepare chromatograms of spots 4, 4a, 6a, 6b and 6c. The second solvent treatment is continued for approximately 15 minutes.

Following treatment with the second solvent, the plate is removed from the solvent container and thoroughly dried, usually in a oven at a relatively low temperature and under vacuum. After the plate has completely dried the chromatograms are visualized by subjecting the layer to fuming 30 percent $SO_3$ at 125° C. for 15-30 minutes. The final resultant visualized chromatograms appear as shown in FIG. 1. The spots remaining at 4, 4a, 6a, 6b and 6c are the heavier asphaltene-like materials contained in the crude oil. Spots 12a, 12b, 12c. 12d and 12e represent the inhibitor, and spots 14a, 14b, 14c, 14d and 14e are the lighter crude oil components which were moved by the hexane solvent. The spots at 12b, 12c and 12d are approximately the same size and have essentially the same intensity, which means that the amount of inhibitor in the crude oil sample is essentially the same as that in the 25 ppm standard, namely 25 ppm.

If the produced fluid is substantially oil, then the concentration of inhibitor in the oil coming from the formation will be 25 ppm. If the produced fluid is a mixture of crude oil and water, it will be necessary to determine the partition coefficient of the inhibitor between the crude oil and water to determine the total amount of inhibitor being produced from the formation.

While perhaps desirable, it is not always possible to send samples of produced fluids to well equipped laboratories where sophisticated analytical procedures and apparatus can be used for preparing chromatograms. It is most desirable to have a procedure which can be utilized in the field, such as on offshore platforms, by personnel who are not highly skilled in testing and analytical procedures.

Figure 2:
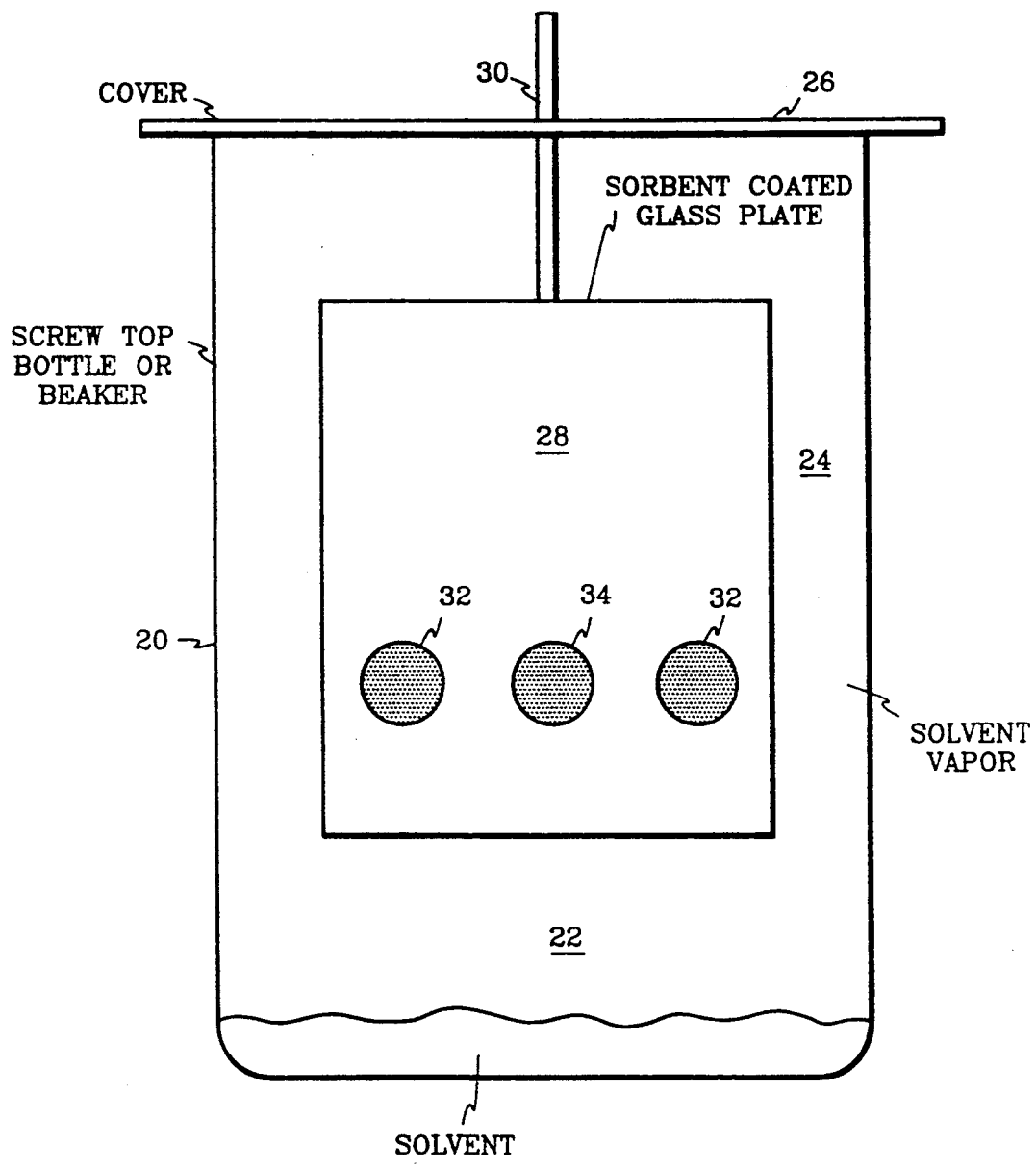
FIG. 2 is a diagram of apparatus used for developing chromatograms in the field.

FIG. 2 is a schematic of a simple apparatus which can be used in the field for the preparation of chromatograms. In carrying out the field procedure, a chromatographic plate 28 is provided with two spots 32 of a standard material which will be used for comparison with the sample of produced fluid. The person carrying out the test will spot the plate at 34 with the produced fluid containing the corrosion inhibitor. The solvent used to develop the samples, preferably a single solvent package, is placed in a wide mouth screw cap bottle or a beaker 20 to maintain a liquid level 22 of about 8 mm. The plate is then placed in the vapor space 24 of the container by a rod or other attachment 30 which passes through cover 26. The plate is maintained in the solvent vapor for a sufficient period of time to equilibrate the absorbent with the solvent vapor. After equilibration the plate is lowered into the solvent 22 to cover the lower portion of the plate below spots 32 and 34 and maintained there for a sufficient period of time to develop the sample chromatograms. The plate is then removed, dried and sprayed with a suitable visualization agent. The visualized chromatogram of the produced oil sample 34 is then compared with the standards developed from spots 32 to determine the relative size and intensity of the inhibitor spot in the produced fluid sample as compared to the inhibitor spot in the standards. When the level of inhibitor in the produced sample is determined to be the same as or below the provided standards, additional inhibitor is squeezed into the reservoir from which the fluids were produced.

If desired, an even more sophisticated portable apparatus could be provided in which separate chambers would hold the solvent or solvents to be used and a timing mechanism could be provided in addition to various other refinements to aid the person preparing the chromatogram.

In the simpliest embodiment of the field technique the spotted plate would be dipped into the solvent without an equilibration step. After a predetermined development time the appearance or lack of appearance of a spot at a prescribed location using the chosen visualization technique would be the determining factor in whether or not to introduce additional inhibitor into the formation.

The following examples are presented in illustration of the invention:

EXAMPLE 1

A thin layer chromatogram was prepared from five samples of terminal water and 1 sample of well water from a gas field. Each sample source had been treated with a commercial corrosion inhibitor package. The major groups of compounds in this inhibitor were 2-alkyl-2-imidazolines and 1-hydroxyethyl-2-alky-2-imidazolines. The inhibitor also contained low molecular weight amines, alcoholic amines, and $C_{16}$ and $C_{18}$ saturated and unsaturated carboxylic acids and amides. A 100 ppm solution of the inhibitor was prepared as a standard.

The sample solutions were applied as spots on a plate having a 250 micron silica gel G layer. Before application of the samples the plate was activated by heating to 120° C. in a vacuum oven at a pressure of 12 inches of mercury. The chromatograms were prepared using a basic organic developing solvent. After development the plate was dried in a hood and then placed in a vacuum oven at 130° C. and a pressure of 12 inches of mercury to dry for 30 minutes. The chromatograms were then visualized by a 20-minute exposure to 30% $SO_3$ fumes at 125° C.

By evaluating the inhibitor spot in the chromatogram of the 100 ppm corrosion inhibitor sample, it was concluded that the detection limit for the inhibitor in this test in a non-oil matrix was approximately 25 ppm (wt/wt). Thus, as the inhibitor package was not detectable in some water samples, their inhibitor value was less than 25 ppm. No inhibitor was detected in four of the samples.

One component of the corrosion inhibitor package was detected in the other two water samples. The compound spot in the water sample chromatograms was larger in diameter than the corresponding spot in the standard (i.e., the organic material in the sample inhibitor spot was more diffuse than that present in the standard inhibitor spot). The intensity of the char fluorescence of this component spot in the two water sample chromatograms was about equal, and was about the same intensity as the spot present in the 100 ppm inhibitor package standard. Thus, it was determined that the concentration of inhibitor in these two terminal water samples was approximately 100 ppm (wt/vol).

EXAMPLE 2

A crude oil containing 10 percent water is produced on an offshore platform. The crude contains the same type corrosion inhibitor as in Example 1. A standard for this inhibitor in crude oil is prepared by adding 2½ milligrams of the inhibitor package to 100 ml of oil and mixing well. This provides a standard containing 25 ppm of the inhibitor package. Before use, one gram of this standard solution is diluted to 10 ml with tetrahydrofuran (or to whatever dilution the samples are being evaluated at). A sample of the produced crude oil, with the water removed, is diluted with tetrahydrofuran in the same manner as the standard sample. Aliquots of the sample and standard solution are then applied to the thin sorbent layer for chromatography. The upper portion of the glass plate is coated with silica gel G 1000 microns thick, and the lower 20% of the plate is coated with kieselguhr. One or more samples of the diluted crude oil are applied as spots along the lower edge of the plate about 1 inch from the bottom in the kieselguhr area. Each spot contains 70 microliters of the spotting solution which is applied to the kieselguhr in small increments with drying time between applications. Spots of the standard solutions are placed on the plate in a similar manner beside the sample spots. After the spots are thoroughly dried of carrier solvent, the plate is placed in the vapor space of a container containing ethyl ether. Thirty minutes is allowed for equilibration of the sorbent material with the ether vapor after which the lower edge of the plate below the spots is immersed in the liquid for a period of 20 to 30 minutes. The plate is then removed from the container and the developing solvent evaporated. The next development is performed in 2-propanol:ammonium hydroxide (8:2, v/v) solvent. After an equilibration period with this solvent the plate is lowered into this second solvent where it is maintained for a period of about 15 minutes. The plate with the chromatograms is removed from the solvent container, briefly air dried and then dried in a vacuum oven at a temperature of 130° C. for 30 minutes at a vacuum of 12 inches of mercury. The plate is then placed on a 125° C. char block, and exposed to 30 percent $SO_3$ fumes in a semi sealed environment at 125° C. for 20 minutes at atmospheric pressure. If the sample chromatograms which are visualized through the sulfur trioxide treatment have a spot at the same relative location and of the same size and intensity as that represented by the corrosion inhibitor standard, this indicates that the amount of inhibitor in the oil produced from the formation is about 25 ppm.

Since the produced oil contains 10 percent water, it is necessary to also determine the amount, if any, of the inhibitor in the water. Partitioning tests are carried out which show that the water contains 3 ppm of inhibitor. Thus the total concentration of inhibitor in the producing well is about 23 ppm. If the cutoff point for adding additional inhibitor to the well is 25 ppm, such addition would be made at this time. Additional samples from the well would be evaluated from time to time to monitor inhibitor levels.

The discussion has been directed to the determination of inhibitor concentration in produced fluids. Where the inhibitor is a complex package quantitation of one or more individual active ingredients may be required. Partitioning coefficients must be determined for the individual moieties of the corrosion inhibitor package.

While the process of the invention finds particular application in controlling corrosion and scale in wells, it may also be applied where produced fluids are being transported through a gathering system or a pipeline. In this type of operation supplemental corrosion or scale inhibitor as required may be added to the flowing produced fluids.

While certain embodiments and details have been shown for the purpose of illustrating the present invention, it will be apparent to those skilled in the art that various changes and modifications may be made herein without departing from the spirit or scope of the invention.

We claim:

1. The process which comprises detecting and quantifying a corrosion or scale inhibitor in a fluid produced form a subterranean formation by subjecting the fluid to thin layer chromatography using one or more solvents to selectively move the inhibitor form the fluid, visualizing chromatograms of the separated inhibitor and thereafter comparing the visualized inhibitor with one or more standards.

2. The process of claim 1 in which the fluid is essentially liquid hydrocarbon (condensate).

3. The process of claim 1 in which the fluid is crude oil.

4. The process of claim 3 in which dual solvents are used to selectively move the inhibitor from the crude oil.

5. The process of claim 1 in which the fluid is mixture of oil and water.

6. The process of claim 5 in which the inhibitor is detected and quantified separately in the oil and water.

7. The process of claim 5 in which the inhibitor is detected and quantified in either the oil or water and the total inhibitor in the two fluids is determined base don prior measurement of the partitioning of the inhibitor between the oil and water phases of the fluid.

8. The process of claim 1 in which the separated inhibitor is visualized by contacting the inhibitor with a chemical reagent.

9. The process of claim 1 in which the separated inhibitor is visualized by $SO_3$ charring.

10. The process which comprises introducing a corrosion inhibitor into a subterranean formation, detecting and qualifying the concentration of the corrosion inhibitor in fluid produced form the subterranean formation by (a) subjecting the fluid to thin layer chromatography using one or more solvents to selectively move the inhibitor from the fluid, (b) visualizing the separated inhibitor, and (c) comparing the visualized inhibitor with one or more standards, and then using such comparison to determine when additional inhibitor is required.

11. The process of claim 10 in which the fluid is essentially liquid hydrocarbon (condensate).

12. The process of claim 10 in which the fluid is crude oil.

13. The process of claim 10 in which the fluid is a mixture of oil and water.

14. The process of claim 13 in which dual solvents are used to selectively move the inhibitor from the oil and water.

15. The process of claim 14 in which the first solvent used is hexane and the second solvent is a mixture of isopropyl alcohol and ammonium hydroxide.

16. The process of claim 10 in which the separated inhibitor is visualized by contacting the inhibitor with a chemical reagent.

17. The process of claim 10 in which the separated inhibitor is visualized by $SO_3$ charring.

18. The process which comprises introducing a corrosion inhibitor into a subterranean formation, detecting the concentration of the corrosion inhibitor in fluid produced form the subterranean formation by (a) subjecting the fluid to thin layer chromatography using one or more solvents to selectively move the inhibitor from the fluid and (b) visualizing the separated inhibitor, and then introducing additional inhibitor into the formation if the separated inhibitor is not visualized at a prescribed concentration.

* * * * *